United States Patent [19]

Ishikawa et al.

[11] 4,390,717
[45] Jun. 28, 1983

[54] PROCESS FOR PREPARING CARBOXYLIC ACID ESTERS OF DICYCLOPENTADIENES

[75] Inventors: Katuhiro Ishikawa, Yokkaichi; Ryotaro Ohno, Tokyo; Masatoshi Arakawa, Yokkaichi, all of Japan

[73] Assignee: Japan Synthetic Rubber Co., Ltd., Tokyo, Japan

[21] Appl. No.: 257,152

[22] Filed: Apr. 24, 1981

[30] Foreign Application Priority Data

Apr. 30, 1980 [JP] Japan ................... 55/57672

[51] Int. Cl.$^3$ ............................................. C07L 67/38
[52] U.S. Cl. ................................................... 560/114
[58] Field of Search ........................ 560/114, 233, 204

[56] References Cited

U.S. PATENT DOCUMENTS

| 2,448,368 | 8/1946 | Gresham | 560/114 |
|---|---|---|---|
| 3,507,891 | 4/1970 | Hearne | 560/233 |
| 3,891,683 | 6/1975 | Isa | 560/233 |
| 3,946,055 | 3/1976 | Isa | 560/233 |
| 3,980,683 | 9/1976 | Isa | 560/233 |
| 3,996,164 | 12/1976 | Matsuda . | |
| 4,048,147 | 9/1977 | Arakawa et al. . | |

FOREIGN PATENT DOCUMENTS 2646955 4/1978 Fed. Rep. of Germany ...... 560/204

OTHER PUBLICATIONS

Falbe, "Carbon Monoxide in Organic Synthesis," pp. 86, 78–85, 99–112 & 177–205, (1970).

Primary Examiner—Michael L. Shippen
Attorney, Agent, or Firm—Oblon, Fisher, Spivak, McClelland & Maier

[57] ABSTRACT

A process for preparing a carboxylic acid ester of a dicyclopentadiene by reacting the dicyclopentadiene with carbon monoxide and an alcohol in the presence of a cobalt compound catalyst, characterized by carrying out said reaction in the presence of 0.5 mole or more of a pyridine base per mole of the dicyclopentadiene at a temperature of 130° C. or less at a carbon monoxide pressure of preferably at least 20 kg/cm$^2$. G to hydroesterify the double bond in the norbornene ring, thereby forming a mono-carboxylate of a dicyclopentadiene, and hydroesterifying the monoesterification product as produced or the isolated monoester to the same reaction conditions as above except that the temperature is 160° C. or less to hydroesterify the remaining double bond of the monoester, thereby forming a dicarboxylate of dicyclopentadiene.

21 Claims, No Drawings

PROCESS FOR PREPARING CARBOXYLIC ACID ESTERS OF DICYCLOPENTADIENES

The present invention relates to a process for preparing a mono- or di-carboxylate of a dicyclopentadiene (DCPD). More particularly, the present invention relates to a process for preparing a mono- or di-carboxylate of a dicyclopentadiene in a high yield by controlling the amount of a pyridine base used and the reaction temperature in the hydroesterification in which a cobalt compound is used as a catalyst.

As the process for the preparation of a mono- or di-carboxylate of a dicyclopentadiene, there has been known a process by which a mono- or di-aldehyde or a mono- or di-methanol of dicyclopentadiene is first synthesized by oxo reaction and the resulting intermediate is oxidized and then esterified. However, said method is disadvantageous in that the procedure is complicated and the yield is low. As a synthesizing method developed based on the studies of oxo reaction, there has been known a hydroesterifying reaction of an olefin with carbon monoxide and an alcohol. Hitherto, when an olefin has been intended to be esterified, the reaction has been carried out in the presence of a catalyst such as cobalt carbonyl, a palladium complex or the like. Since this kind of reaction is usually conducted at a high temperature, the application of this technique to dicyclopentadienes has the defect that side reactions due to the pyrolysis of dicyclopentadienes take place, resulting in the lowering of the yield.

The present inventors have found that a mono- or di-carboxylate of a dicyclopentadiene can be obtained in a high yield from the dicyclopentadiene by hydroesterification using a cobalt compound as a catalyst, and have made a further extensive study to establish an industrially practicable method. As a result, it has been found that:

(1) a side reaction characteristic of the double bond in the norbornene ring can be suppressed by adding at least a certain amount of a pyridine base to the reaction system based upon the dicyclopentadiene, (2) by carrying out the hydroesterification of a dicyclopentadiene at a relatively low temperature of 130° C. or below, various side reactions due to the pyrolysis of dicyclopentadiene can be prevented and a monocarboxylate of a dicyclopentadiene can be obtained in a high yield, (3) by subjecting the monocarboxylate thus obtained to the second hydroesterification, a dicarboxylate of the dicyclopentadiene can be obtained in a high yield, (4) in this case, the reaction rate can be increased by carrying out the second hydroesterification at a temperature of at least 130° C., and (5) by maintaining the carbon monoxide pressure at 20 kg/cm$^2$.G or higher in the preparation of the monocarboxylate, the side reaction characteristic of the double bond of the norbornene ring is more effectively suppressed to enable the mono- or di-carboxylate of the dicyclopentadiene to be obtained in a higher yield.

Based on this finding, an industrially very advantageous production process has been established.

According to the present invention, there is provided a process for preparing a mono- or di-carboxylate of a DCPD in a high yield, by reacting the DCPD with carbon monoxide and an alcohol in the presence of a cobalt compound catalyst through the following route:

dicarboxylate of DCPD, characterized by carrying out the first hydroesterification (step (1)) at a temperature of not more than 130° C. in the presence of a pyridine base in a proportion of at least 0.5 mole per mole of the DCPD to prevent various side reactions due to the pyrolysis of the DCPD, particularly side reactions characteristic of the double bond of the norbornene ring to produce the monocarboxylate in a high yield, and subjecting the monocarboxylate of a DCDP thus obtained to the second hydroesterification (step (2)) at a temperature of preferably 130° C. or higher.

Further, in the process for preparing a monocarboxylate of a DCPD according to the present invention, the side reactions characteristic of the double bond of the norborne ring are more effectively suppressed by maintaining the carbon monoxide pressure at 20 kg/cm$^2$.G or more, whereby the mono- or di-carboxylate of the dicyclopentadiene can be prepared in a higher yield.

The term "pyridine base" used herein is the collective name of pyridine and its homologues, including methyl derivatives such as $\beta$-picoline, $\gamma$-picoline and the like; ethyl derivatives such as 4-ethylpyridine and the like; dimethyl derivatives such as 3,4-lutidine, 3,5-lutidine, and the like; trimethyl derivatives and methylethyl derivatives such as $\beta$-collidine, and the like. Isoquinoline is also usable as the pyridine base in the present invention. Particularly, pyridine and picoline are preferable as the pyridine base. The pyridine base contributes to the suppression of the afore-said various side reactions and, at the same time, acts as a catalyst for the hydroesterification in the form of a complex with the cobalt compound.

It is required for the purpose of suppressing the side reactions of the starting dicyclopentadienes that the pyridine base be added in an amount of 0.5 mole or more, preferably 0.8 mole or more per mole of the dicyclopentadienes. If it is less than 0.5 mole, it is difficult to suppress the side reactions characteristic of the double bond of the norbornene ring, and consequently, the yield of mono- or di-carboxylate of a dicyclopentadiene is lowered. The above-mentioned condition is necessary in the case of the first hydroesterification, namely, in the preparation of the monocarboxylate, and the amount of the pyridine base is not critical in the second hydroesterification. On the other hand, there is no upper limit on the amount of the pyridine base, but the use of an excessively large amount of pyridine base leads to reduction of the reaction rate and has no practical significance. Usually it is preferred to use 2.0 moles or less of the pyridine base.

The reaction conditions, which are the second requirement of the present invention, are characterized by carrying out the first hydroesterification at a relatively low temperature. The reaction temperature in the first hydroesterification, that is, mainly the hydroesterification of the double bond of the norbornene ring, is in the range of from 80° to 130° C., preferably 100° to 120° C. If the first step reaction is carried out at a temperature of at least 130° C., side reactions due to pyrolysis of a DCPD take place and monocarboxylate cannot be obtained in a high yield. The temperature condition in the second hydroesterification for preparing a dicarboxylate, that is, hydroesterification of the remaining double bond, is in the range of from 100° to 160° C., preferably 120° to 160° C., more preferably 130° to 150° C. The reaction rate can be increased by elevating the reaction temperature in the second step to 130° C. or higher. In the production of a dicarboxylate, the first hydroesterification and the second hydroesterification may be carried out in succession or alternatively, the second hydroesterification may be carried out after the removal of the unreacted dicyclopentadiene in the first hydroesterification products, or the second hydroesterification may be carried out discontinuously in such a manner that the monocarboxylate of a dicyclopentadiene is separated from the reaction product of the first hydroesterification and said monocarboxylate is subjected to the second hydroesterification. The first hydroesterification and the second hydroesterification may be carried out either at the predetermined temperature in the said range or while elevating the temperature continuously. When the second hydroesterification is carried out by elevating the temperature immediately after the first hydroesterification has been completed, it is preferable that 80% or more of the double bond of the norbornene ring is reacted in the first hydroesterification. On the other hand, when the first hydroesterification and the second hydroesterification are not carried out continuously, it is not required that the first hydroesterification is effected until 80% or more of the double bond of the nobornene ring is reacted, because unreacted dicyclopentadiene is removed after the first hydroesterification.

Among the reaction conditions, the carbon monoxide pressure during the reaction is not critical. However, it is preferably 20 kg/cm$^2$.G or more from the viewpoint of catalyst stability and the yield. Particularly in the first hydroesterification, namely, in the preparation of a monocarboxylate, the carbon monoxide pressure is preferably 20 kg/cm$^2$.G or more, more preferably 50 kg/cm$^2$.G or more, for the purpose of suppressing the side reactions characteristic of the double bond of the norbornene ring. By increasing the carbon monoxide pressure, suppression of the side reactions characteristic of the double bond of the norbornee ring is promoted and the said effect is rapidly increased when the pressure exceeds 20 kg/cm$^2$.G. However, even if the pressure is elevated to more than 200 kg/cm$^2$.G, the effect thereof is not significant.

As the carbon monoxide source to be fed to the reaction system, it is preferable to employ carbon monoxide having a hydrogen content as low as possible, because the carbon monoxide having a high hydrogen content such as water gas promotes the formation of an aldehyde as by-product, resulting in lowering the yield.

As the starting dicyclopentadiene used in the present invention, it is the matter of course that suitable dicyclopentadienes may be selected depending on the desired mono- or di-carboxylate, though dicyclopentadiene, dimethyldicyclopentadiene and the like may be usually used.

As the alcohols, there may be used monohydric alcohols such as methyl alcohol, ethyl alcohol, propyl alcohol and the like and polyhydric alcohols such as ethylene glycol, propylene glyocl, glycerin, pentaerythritol and the like. Though the ratio of the di-cyclopentadiene to the alcohol may be freely selected, it is generally preferably to use 1.0 to 3.0 moles of the alcohol in the method for the preparation of a monocarboxylate and 1.5 to 5.0 moles of the alcohol in the methodd for the preparation of dicarboxylate, respectively, per mole of the dicyclopentadiene. In the method for the preparation of a dicarboxylate, the alcohol may be added to the reaction system either at once at the initial stage of the reaction or in two portions, that is, at the initial stage of the reaction and after completion of the first hydroesterification. However, when the alcohol is added in two portions, the amount of the alcohol added at the initial stage must be 1.0 mole or more per mole of the dicyclopentadiene.

As the cobalt compound acting effectively as a catalyst in the co-existence with a pyridine base, there may be used a cobalt carbonyl, or a cobalt compound capable of forming a cobalt carbonyl such as cobalt oxide, cobalt carbonate, cobalt hydroxide, metallic cobalt, cobalt acetate, cobalt napthenate, cobalt octenate, and the like. When a cobalt compound capable of forming a cobalt carbonyl is used, a preliminary step for converting it to a cobalt carbonyl is required.

Though the ratio of the pyridine base to the cobalt compound is not critical, it is preferable to use 1.5 to 4.0 moles of the pyridine base per gram atom of cobalt in the cobalt compound because the catalyst is easily separated from the reaction product after completion of the reaction.

As the solvent in the process of the present invention, there may be used hydrocarbons such as pentane, hexane, heptane, cyclohexane, benzene, toluene, xylene and the like and polar compounds such as acetone, tetrahydrofurane, methyl ethyl ketone, methyl acetate and the like. Though the amount of the solvent is not critical, it is preferable to use the solvent in an amount of 0 to 2 times the volume of dicyclopentadienes.

After the reaction is completed, the catalyst can be separated easily by adding to the reaction mixture hydrocarbons such as pentane, hexane, heptane, cyclohexane, benzene, toluene, xylene and the like. The catalyst as separated can be recycled to the reaction system for reuse without any particular treatment or after activation. An operation such as separation or the like should be effected under an inert atmosphere such as carbon monoxide, nitrogen or the like in order to prevent the decomposition of the catalyst.

According to the present invention, the mono- or di-carboxylate of a dicyclopentadiene can be obtained in a high yield and, moreover, the catalyst can be separated and recycled for reuse after completion of the reaction, and hence, the present process is very advantageous in industry.

The mono- or di-carboxylate of a dicyclopentadiene obtained according to the process of the present invention has an advantage that when the carboxylate is used as a basic acid component in an unsaturated polyester resin, an unsaturated polyester resin coating material, an alkyd resin coating material, an oil-free alkyd resin coating material or the like, there can be improved remarkably the boiling water resistance, chemical resistance, water resistance, flexibility, impact resistance, heat resistance, wheather resistance, and air-dryability as compared with those containing phthalic anhydride, isophthalic acid, terephthalic acid, fatty acid and the like as the basic acid component. The carboxylate of a dicyclopentadiene of the present invention is a cycloaliphatic carboxylate and has a great industrial value when used as a modifier for saturated polyester, a plasticizer or a lubricant.

The present invention is illustrated below referring to Examples, but these Examples are only by way of illustration and not by way of limitation.

EXAMPLE 1 (Preparation of Monocarboxylate)

Into a 5-liter autoclave were charged 6 moles of dicyclopentadiene, 6.6 moles of methyl alcohol, 7.5 moles of pyridine and 1.5 moles of dicobalt octacarbonyl, and carbon monoxide was introduced thereinto to a pressure of 50 kg/cm$^2$.G, after which the reaction mixture was heated to 110° C. to carry out the reaction. While maintaining the carbon monoxide pressure at 50 kg/cm$^2$.G by supplying an amount of carbon monoxide corresponding to the amount of the carbon monoxide consumed by the reaction from the exterior, hydroesterification of the double bond of the norbornene ring was carried out for 3 hours.

After cooling, carbon monoxide was removed and the reaction mixture was treated with 3 N aqueous hydrochloric acid solution to decompose the catalyst, washed with water and then subjected to distillation under reduced pressure to obtain 80 g of the fraction at 30° to 40° C./1 mm Hg (dicyclopentadiene) and 945 g of the fraction at 80° to 90° C./1 mm Hg (methyl tricyclodecenemonocarboxylate). The saponification value of this fraction at 80° to 90° C./1 mm Hg was 290, which agreed with the saponification value of methyl tricyclodecenemonocarboxylate, 292. The product was also confirmed to be methyl tricyclodecenemonocarboxylate by GPC, NMR and IR.

From the result of distillation, it was found that the conversion of dicyclopentadiene was 90 mole% and the yield of methyl tricyclodecenemonocarboxylate was 82 mole%. The methyl tricyclodecenemonocarboxylate was a transparent colorless liquid having a viscosity of 14 centipoises (at 20° C.).

EXAMPLE 2

The same procedure as in Example 1 was repeated, except that the carbon monoxide pressure was reduced from 50 kg/cm$^2$.G to 30 kg/cm$^2$.G. It was found from the distillation result that the conversion of dicyclopentadiene was 91 mole% and the yield of methyl tricyclodecenenomocarboxylate was 76 mole%.

EXAMPLE 3

The same procedure as in Example 1 was repeated, except that the amount of pyridine was changed from 7.5 moles to 4.8 moles. It was found from the distillation result that the conversion of dicyclopentadiene was 97 mole% and the yield of methyl tricyclodecenemonocarboxylate was 75 mole%.

COMPARATIVE EXAMPLE 1

Reaction was carried out in the same way as in Example 1, except that the reaction temperature was 135° C. and the reaction time was 1 hour. It was found from the distillation result that the conversion of dicyclopentadiene was 98 mole% and the yield of methyl tricyclodecenemonocarboxylate was 48 mole%.

COMPARATIVE EXAMPLE 2

Reaction was carried out in the same manner as in Example 1, except that the amount of pyridine was changed from 7.5 moles to 2.5 moles and the amount of dicobalt octacarbonyl was changed from 1.5 moles to 0.5 mole. It was found from the distillation result that the conversion of dicyclopentadiene was 83 mole% and the yield of methyl tricyclodecenemonocarboxylate was 38 mole%.

EXAMPLE 4 (Preparation of Dicarboxylate)

Into a 5-liter autoclave were charged 6 moles of dicyclopentadiene, 15 moles of methyl alcohol, 7.5 moles of pyridine and 1.5 moles of dicobalt octacarbonyl, and carbon monoxide was introduced thereinto to a pressure of 50 kg/cm$^2$.G, and the reaction mixture was heated to 110° C. to conduct the reaction. While maintaining the carbon monoxide pressure at 30 kg/cm$^2$.G by supplying an amount of carbon monoxide corresponding to the amount of carbon monoxide consumed by the reaction from the exterior, the reaction was carried out for 3 hours until the hydroesterification conversion of the double bond of the norbornene ring reached 90%. Thereafter, the reaction temperature was raised to 140° C. and the reaction was carried out at said temperature for a further 3 hours.

After cooling, the carbon monoxide was removed and the reaction mixture was treated with 3 N aqueous hydrochloric acid solution to decompose the catalyst, washed with water, and then subjected to distillation under reduced pressure to obtain 138 g of the fraction at 80° to 90° C./1 mm Hg (methyl tricyclodecenemonocarboxylate) and 1,224 g of the fraction at 135° to 140° C./1 mm Hg (dimethyl tricyclodecanedicarboxylate). The latter fraction at 135° to 140° C./1 mm Hg had a saponification value of 443, which agreed with that of dimethyl tricyclodecanedicarboxylate (444). It was confirmed from the determination of GPC, NMR and IR that the said distillate was dimethyl tricyclodecanedicarboxylate.

From the result of distillation, it was found that the conversion of dicyclopentadiene was 100 mole%, the yield of methyl tricyclodecenemonocarboxylate was 12 mole% and the yield of dimethyl tricyclodecanedicarboxylate was 81 mole%. The dimethyl tricyclodecanedicarboxylate thus obtained was a transparent, colorless liquid having a viscosity of 65 cps (centipoises) at 20° C. and a diffraction $n_D^{20}$ of 1.497.

EXAMPLE 5

Into a 5-liter autoclave were charged 3.0 moles of cobalt oxide and 3.0 moles of pyridine. Hydrogen was introduced thereinto to a pressure of 20 kg/cm$^2$.G and then carbon monoxide was introduced thereinto to a pressure of 80 kg/cm$^2$.G, after which reaction was carried out at 160° C. for 2 hours to synthesize cobalt carbonyl.

After cooling, the hydrogen and carbon monoxide were removed and 4.0 moles of pyridine, 6.0 moles of dicyclopentadiene and 15 moles of methanol were charged into the autoclave. Carbon monoxide was introduced thereinto to a pressure of 50 kg/cm$^2$.G and the first hydroesterification was carried out at 110° C. for 3 hours and the second hydroesterification was carried out at 140° C. for 3 hours in the same way as in Example 1.

From the result of distillation, it was found that the conversion of dicyclopentadiene was 100 mole%, the yield of methyl tricyclodecenemonocarboxylate was 14 mole% and the yield of dimethyl tricyclodecanedicarboxylate was 78 mole%.

EXAMPLE 6

In Example 4, the first hydroesterification was carried out at 120° C. and the second hydroesterification was carried out at 150° C., each for 2 hours.

From the result of distillation, it was found that the conversion of dicyclopentadiene was 100 mole%, the yield of methyl tricyclodecenemonocarboxylate was 10 mole% and the yield of dimethyl tricyclodecanedicarboxylate was 80 mole%.

EXAMPLE 7

In Example 4, 800 ml of cyclohexane was used as the reaction solvent.

From the result of distillation, it was found that the conversion of dicyclopentadiene was 100 mole%, the yield of methyl tricyclodecenemonocarboxylate was 8 mole% and the yield of dimethyl tricyclodecanedicarboxylate was 86 mole%.

EXAMPLE 8

Into a 5-liter autoclave were charged 6 moles of dicyclopentadiene, 9 moles of methanol, 7.5 moles of pyridine and 1.5 moles of dicobalt octacarbonyl. Carbon monoxide was introduced thereinto to a pressure of 50 kg/cm$^2$.G and the reaction mixture was heated to 110° C. to effect reaction for 3 hours. The carbon monoxide pressure was maintained at 30 kg/cm$^2$.G by supplying carbon monoxide in an amount corresponding to the amount of carbon monoxide consumed by the reaction from the exterior. After cooling, carbon monoxide was removed and the reaction mixture was fed to 5 liters of cyclohexane. After stirring, the reaction mixture was allowed to stand to separate it into the reaction product and the catalyst. The reaction product was subjected to distillation under reduced pressure to obtain 127 g of the fraction at 30° to 40° C./1 mm Hg (dicyclopentadiene), 683 g of the fraction at 80° to 90° C./1 mm Hg (methyl tricyclodecenemonocarboxylate) and 38 g of the fraction at 135° to 140° C./1 mm Hg (dimethyl tricyclodecanedicarboxylate).

Into the autoclave were charged 683 g (3.5 moles) of the methyl tricyclodecenemonocarboxylate thus obtained, 6 moles of methanol and 70% of the catalyst previously separated (2.1 moles of cobalt and 4.7 moles of pyridine), and carbon monoxide was introduced thereinto to a pressure of 50 kg/cm$^2$.G. The reaction was carried out at 140° C. for 3 hours. After cooling, carbon monoxide was removed and the reaction mixture was treated with a 3 N aqueous hydrochloric acid solution to decompose the catalyst. After washing with water, the reaction mixture was subjected to distillation under reduced pressure to obtain 124 g of the fraction at 80° to 90° C./1 mm Hg (methyl tricyclodecenemonocarboxylate) and 899 g of the fraction at 135° to 140° C./1 mm Hg (dimethyl tricyclodecanedicarboxylate).

From the result of distillation, it was found that the conversion of dicyclopentadiene was 84 mole%, the yield of methyl tricyclodecenemonocarboxylate was 11 mole%, and the yield of dimethyl tricyclodecanedicarboxylate was 68 mole%.

EXAMPLE 9

In Example 4, the reaction mixture as produced was fed to 5 liters of cyclohexane under a nitrogen atomsphere and the resulting mixture was stirred and allowed to stand, upon which the catalyst was separated in the lower layer. The amount of cobalt contained in the catalyst was 99.8% of the amount of cobalt charged and the amount of pyridine was 89.2% of that of pyridine charged.

To the catalyst separated were added 6 moles of dicyclopentadiene, 15 moles of methanol and 0.8 mole of pyridine, and reaction was carried out in a similar manner to that in Example 4.

From the result of distillation, it was found that the conversion of dicyclopentadiene was 100 mole%, the yield of methyl tricyclodecenemonocarboxylate was 13 mole%, and the yield of dimethyl tricyclodecanedicarboxylate was 78 mole%.

EXAMPLE 10

Into a 5-liter autoclave were charged 2 moles of dicyclopentadiene, 5 moles of methanol, 2.5 moles of pyridine and 0.5 mole of dicobalt octacarbonyl were charged. Carbon monoxide was introduced thereinto to a pressure of 50 kg/cm$^2$.G and then the contents were heated to 110° C. to effect reaction. While maintaining the carbon monoxide pressure at 30 kg/cm$^2$.G by supplying carbon monoxide in an amount corresponding to the carbon monoxide consumed by the reaction from the exterior, the reaction was carried out for 3 hours until the hydroesterification conversion of the double bond of the norbornene ring reached 90%. Thereafter, 2 moles of dicyclopentadiene and 5 moles of methanol were fed under pressure under the reaction conditions and the reaction was carried out for 3 hours in the same manner. Further, 2 moles of dicyclopentadiene and 5 moles of methanol were fed under pressure and the reaction was carried out for 3 hours in the same way. Thereafter, the reaction temperature was elevated to 140° C. and the reaction was carried out for a further 3 hours.

After cooling, the carbon monoxide was removed and the reaction mixture was treated with a 3 N aqueous hydrochloric acid solution to decompose the catalyst washed with water, and then subjected to distillation under reduced pressure.

From the result of distillation, it was found that the conversion of dicyclopentadiene was 100 mole%, the yield of methyl tricyclodecenemonocarboxylate was 8 mole%, and the yield of dimethyl tricyclodecanedicarboxylate was 80 mole%.

EXAMPLE 11

The same procedure as in Example 4 was repeated, except that the reaction temperature was altered from 140° C. to 125° C. and the reaction time was prolonged from 3 hours to 6 hours, to effect the reaction.

From the result of distillation, it was found that the conversion of dicyclopentadiene was 100 mole%, the yield of methyl tricyclodecenemonocarboxylate was 16 mole%, and the yield of dimethyl tricyclodecanedicarboxylate was 77 mole%.

COMPARATIVE EXAMPLE 3

In Example 4, the reaction temperature was kept at 140° C. throughout the first hydroesterification and the second hydroesterification and the reaction was carried out for a total of 4 hours.

From the result of distillation, it was found that the conversion of dicyclopentadiene was 100 mole%, the yield of methyl tricyclodecenemonocarboxylate was 12 mole%, and the yield of dimethyl tricyclodecanedicarboxylate was 60 mole%.

COMPARATIVE EXAMPLE 4

The same procedure as in Example 4 was repeated, except that the amount of pyridine was reduced from 7.5 moles to 2.5 moles and the amount of dicobalt octacarbonyl was reduced from 1.5 moles to 0.5 mole.

From the result of distillation, it was found that the conversion of dicyclopentadiene was 100 mole%, the yield of methyl tricyclodecenemonocarboxylate was 6 mole%, and the yield of dimethyl tricyclodecanedicarboxylate was 54 mole%.

In Examples 4 to 11, a monocarboxylate of a dicyclopentadiene which is an intermediate product from the dicyclopentadiene to a dicarboxylate thereof, was formed partially. Since said intermediate can be separated easily from the dicarboxylate by distillation, the yield of the dicarboxylate can further be increased by returning said intermediate to the reaction system after separation.

What is claimed is:

1. A process for preparing a monocarboxylic ester of a dicyclopentadiene by reacting the dicyclopentadiene with carbon monoxide at a pressure of at least 30 kg/cm$^2$ and an alcohol in the presence of a cobalt compound catalyst, characterized by carrying out said reaction at a temperature of 130° or less in the presence of a pyridine base in an amount of 0.5 mole or more per mole of the dicyclopentadiene to hydroesterify the double bond of the norbornene ring.

2. A process for preparing a dicarboxylic ester of a dicyclopentadiene by reacting the dicyclopentadiene with carbon monoxide at a pressure of at least 30 kg/cm$^2$ and an alcohol in the presence of a cobalt compound catalyst, characterized by carrying out said reaction at a temperature of 130° C. or less in the presence of a pyridine base in an amount of 0.5 mole or more per mole of the dicyclopentadiene to hydroesterify the double bond of the norbornene ring, thereby preparing a monocarboxylic ester of the dicyclopentadiene, and subsequently hydroesterifying the remaining double bond of said ester to prepare a dicarboxylic ester of the dicyclopentadiene.

3. A process for preparing a dicarboxylic ester of a dicyclopentadiene by reacting the dicyclopentadiene with carbon monoxide at a pressure of at least 30 kg/cm$^2$ and an alcohol in the presence of a cobalt compound catalyst, characterized by carrying out said reaction at a temperature of 130° C. or lower in the presence of a pyridine base in an amount of 0.5 mole or more per mole of the dicyclopentadiene, and subsequently elevating the temperature of the reaction system to more than 130° C. to allow the reaction to proceed.

4. A process according to claim 1, wherein the hydroesterification is carried out at a temperature ranging from 80° to 130° C.

5. A process according to claim 1, wherein the hydroesterification is carried out at a temperature ranging from 100° to 120° C.

6. A process according to claim 2 or 3, wherein the first hydroesterification is carried out at a temperature ranging from 80° to 130° C.

7. A process according to claim 2 or 3, wherein the first hydroesterification is carried out at a temperature ranging from 100° to 120° C.

8. A process according to claim 6, wherein the second hydroesterification is carried out at a temperature ranging from 100° to 160° C.

9. A process according to claim 7, wherein the second hydroesterification is carried out at a temperature ranging from 130° to 150° C.

10. A process according to claim 3, wherein the first hydroesterification is carried out until 80% or more of the double bond of the norbornene ring is hydroesterified.

11. A process according to claim 1, 2 or 3, wherein the pyridine base is pyridine.

12. A process according to claim 1, 2 or 3, wherein the pyridine base is a pyridine homologue selected from the group consisting of methyl derivatives, ethyl derivatives, dimethyl derivatives, trimethyl derivatives and methyl-ethyl derivatives of pyridine.

13. A process according to claim 1, 2 or 3, wherein the pyridine base is a pyridine homologue selected from the group consisting of β-picoline, γ-picoline, 4-ethylpyridine, 3,4-lutidine, and β-collidine.

14. A process according to claim 1, 2 or 3, wherein the amount of the pyridine base is at least 0.8 mole per mole of the dicyclopentadiene.

15. A process according to claim 1, 2 or 3, wherein the cobalt compound is cobalt carbonyl.

16. A process according to claim 1, 2 or 3, wherein the cobalt compound is a compound selected from the group consisting of cobalt oxide, cobalt carbonate, cobalt hydroxide, metallic cobalt, cobalt acetate, cobalt naphthenate, and cobalt octenate.

17. A process according to claim 15, wherein the proportion of the pyridine base to the cobalt compound is 1.5 to 4.0 moles of pyridine base per gram-atom of cobalt in the cobalt compound.

18. A process according to claim 16, wherein the proportion of the pyridine base to the cobalt compound is 1.5 to 4.0 moles of pyridine base per gram-atom of cobalt in the cobalt compound.

19. A process according to claim 1, 2 or 3, wherein the alcohol is a member selected from the group consisting of methyl alcohol, ethyl alcohol, propyl alcohol, ethylene glycol, propylene glycol, glycerin, and pentaerythritol.

20. A process according to claim 1, wherein the proportion of the alcohol to the dicyclopentadiene is 1.0 to 3.0 moles per mole of the dicyclopentadiene.

21. A process according to claim 2 or 3, wherein the proportion of the alcohol to the dicyclopentadine is 1.5 to 5.0 moles per mole of the dicyclopentadiene.

* * * * *